United States Patent

Korsgaard et al.

Patent Number: 6,008,242
Date of Patent: *Dec. 28, 1999

[54] USE OF 1-CENTCHROMAN FOR THE MANUFACTURE OF A PHARMACEUTICAL COMPOSITION FOR THE TREATMENT OF OBESITY

[75] Inventors: Niels Korsgaard, Værløse; Michael Shalmi, København V; Steven Bain, Birkerød; Birgitte Hjort Guldhammer, Hillerød, all of Denmark

[73] Assignee: Novo Nordisk A/S, Bagsvaerd, Denmark

[*] Notice: This patent issued on a continued prosecution application filed under 37 CFR 1.53(d), and is subject to the twenty year patent term provisions of 35 U.S.C. 154(a)(2).

[21] Appl. No.: 08/585,013

[22] Filed: Jan. 11, 1996

[30] Foreign Application Priority Data

Jan. 20, 1995 [DK] Denmark ................ 0066/95
Jun. 30, 1995 [DK] Denmark ................ 0774/95

[51] Int. Cl.$^6$ .................................. A61K 31/40
[52] U.S. Cl. ................ 514/422; 514/456; 514/909; 514/910
[58] Field of Search ........................ 514/456, 422

[56] References Cited

U.S. PATENT DOCUMENTS

| | | | |
|---|---|---|---|
| 3,822,287 | 7/1974 | Bolger | 260/326.5 D |
| 4,447,622 | 5/1984 | Salman et al. | 548/525 |
| 5,280,040 | 1/1994 | Labroo et al. | 514/422 |

OTHER PUBLICATIONS

Chak et al., "Acute Toxicity & Pharmacology of Centchroman", Indian Journal of Experimental Biology, vol. 15, Dec. 1977, pp. 1159–1161.

Ray et al., "An X–ray Crystallographic Study of the Nonsterodial Contraceptive Agent Centchroman", J. Med. Chem. Soc., vol. 37, pp. 696–700, 1994.

*Primary Examiner*—M. Moezie
*Attorney, Agent, or Firm*—Steve T. Zelson; Cheryl H. Agus

[57] ABSTRACT

The present invention provides novel uses of compounds of general formula I

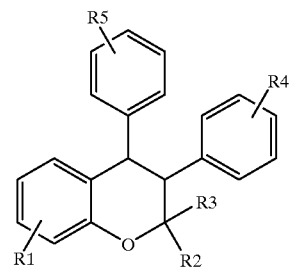

wherein $R^1$, $R^4$ and $R^5$ are individually hydrogen, hydroxy, halogen, trifluoromethyl, lower alkyl, lower alkoxy or (tertiary amino)(lower alkoxy); and $R^2$ and $R^3$ are individually hydrogen or lower alkyl, or as a pharmaceutically acceptable salt thereof in combination with a pharmaceutically acceptable carrier for the manufacture of a pharmaceutical composition for the treatment or-prophylaxis of obesity.

3 Claims, No Drawings

USE OF 1-CENTCHROMAN FOR THE MANUFACTURE OF A PHARMACEUTICAL COMPOSITION FOR THE TREATMENT OF OBESITY

FIELD OF THIS INVENTION

The present invention relates to the use of compounds of the general formula I for the treatment of patients suffering from obesity and prophylaxis hereof. The present invention also embraces pharmaceutical compositions comprising these compounds and methods of using the compounds and their pharmaceutical compositions.

BACKGROUND OF THIS INVENTION

Obesity is a well known risk factor for the development of many very common diseases such as atherosclerosis, hypertension and diabetes. The incidence of obese people and thereby also these diseases is increasing throughout the entire industrialised world. Except for exercise, diet and food restriction no convincing pharmacologic treatment for reducing body weight effectively and acceptably currently exist. However, due to its indirect but important effect as a risk factor in mortal and common diseases it will be important to find treatment for obesity.

The term obesity implies an excess of adipose tissue. In this context obesity is best viewed as any degree of excess adiposity that imparts a health risk. The cutoff between normal and obese individuals can only be approximated, but the health risk imparted by the obesity is probably a continuum with increasing adiposity. The Framingham study demonstrated that a 20% excess over desirable weight clearly imparted a health risk. (Mann GV N. Engl. J.Med 291:226, 1974). In the United States a National Institutes of Health consensus panel on obesity agreed that a 20% increase in relative weight or a body mass index (BMI =body weight in kilograms divided by height in meters) above the 85th percentile for young adults constitutes a health risk. By the use of these criteria 20 to 30 percent of adult men and 30 to 40 percent of adult women in the United States are obese. (NIH, Ann Intern Med 103:147, 1985).

Even mild obesity increases the risk for premature death, diabetes, hypertension, atherosclerosis, gallbladder disease and certain types of cancer. In the industrialized western world the prevalence of obesity has increased significantly in the past few decades. Because of the high prevalence of obesity and its health consequences, its prevention and treatment should be a high public health priority.

When energy intake exceeds expenditure, the excess calories are stored in adipose tissue, and if this net positive balance is prolonged, obesity results, i.e. there are two components to weight balance, and an abnormality on either side (intake or expenditure) can lead to obesity.

The regulation of eating behaviour is incompletely understood. To some extent appetite is controlled by discrete areas in the hypothalamus: a feeding center in the ventrolateral nucleus of the hypothalamus (VLH) and a satiety center in the ventromedial hypothalamus (VMH). The cerebral cortex receives positive signals from the feeding center that stimulate eating, and the satiety center modulates this process by sending inhibitory impulses to the feeding center. Several regulatory processes may influence these hypothalamic centres. The satiety center may be activated by the increases in plasma glucose and/or insulin that follow a meal. Meal-induced gastric distension is another possible inhibitory factor. Additionally the hypothalamic centres are sensitive to cate-cholamines, and beta-adrenergic stimulation inhibits eating behaviour. Ultimatively, the cerebral cortex controls eating behaviour, and impulses from the feeding center to the cerebral cortex are only one input. Psychological, social, and genetic factors also influence food intake.

At present a variety of techniques are available to effect initial weight loss. Unfortunately, initial weight loss is not an optimal therapeutic goal. Rather, the problem is that most obese patient eventually regain their weight. An effective means to establish and/or sustain weight loss is the major challenge in the treatment of obesity today.

Centchroman is a non-steroidal compound known to have antiestrogenic activity. It is in use in India as an oral contraceptive (see, for example, Salman et al., U.S. Pat. No. 4,447,622; Singh et al., Acta Endocrinol. (Copenh) 126 (1992), 444–450; Grubb, Curr.Opin.Obstet. Gynecol. 3 (1991), 491–495; Sankaran et al., Contraception 9 (1974), 279–289; Indian Patent Specification No. 129187). Centchroman has also been investigated as an anti-cancer agent for treatment of advanced breast cancer (Misra et al., W. J. Cancer 43 (1989), 781–783). Recently, centchroman as a racemate has been found potent as a cholesterol lowering pharmaceutical expressed by a significant decrease of the serum concentrations (S.D. Bain et al., J.Min.Bon.Res. 9 (1994), 394.

U.S. Pat. No. 5,280,040 describes methods and pharmaceutical compositions for reducing bone loss using 3,4-diarylchromans and their pharmaceutically acceptable salts.

Thus there remains today a need in the art for compositions and methods that are useful in the treatment or prophylaxis of obesity.

One object of the present invention is to provide compounds which can effectively be used in the treatment or prophylaxis of obesity.

BRIEF DESCRIPTION OF THIS INVENTION

It has, surprisingly, been found that compounds of the general formula I as stated in claim 1 can be used in the treatment or prophylaxis of obesity.

DETAILED DESCRIPTION OF THIS INVENTION

The present invention is based in part on the discovery that a representative 3,4-diarylchroman, centchroman (3,4-trans-2, 2-dimethyl-3-phenyl-4-[4-(2-(pyrrolidin- 1-yl) ethoxy)phenyl]-7-methoxychroman) is effective against obesity, inter alia in rabbits. Centchroman is a racemic mixture. These animal models are generally recognized models of obesity. These data thus indicate that the 3,4diarylchromans of formula I are useful as therapeutic agents against obesity in mammals, including primates such as humans.

Within the present invention, compounds of formula I as stated in claim 1 are used against obese patients. Within formula I,$R^1$, $R^4$ and $R^5$ are individually hydrogen, halogen, trifluoromethyl, lower alkyl, lower alkoxy or (tertiary amino)(lower alkoxy); and $R^2$ and $R^3$ are individually hydrogen or a lower alkyl. As used herein, the term "lower alkyl" includes straight and branched chain alkyl radicals containing from 1 to 6 carbon atoms, such as methyl, ethyl, n-propyl, isopropyl, n-butyl, tert-butyl, n-amyl, sec-amyl, n-hexyl, 2-ethylbutyl, 2,3-dimethylbutyl and the like. The term "lower alkoxy" includes straight and branched chain alkoxy radicals containing from 1 to 6 carbon atoms, such as methoxy, ethoxy, n-propoxy, isopropoxy, n-butoxy, tert-butoxy, n-amyloxy, sec-amyloxy, n-hexyloxy, 2-ethylbutoxy, 2,3-dimethylbutoxy and the like. "Halogen" includes chloro, fluoro, bromo and iodo. The tertiary amino radical may be a N,N-dialkylamine such as a N,N-dimethylamino, N,N-diethylamino, N,N-dipropylamino and N,N-dibutylamino or a polymethyleneimine, e.g., piperidine, pyrrolidine, N-methylpiperazine or morpholine. Herein, the term "(tertiary amino)(lower alkoxy)" is a lower alkoxy group which is substituted by a tertiary amino group. Preferred compounds include those in which $R^1$ is lower alkoxy; $R^2$ and $R^3$ are lower alkyl, especially methyl; $R^4$ is hydrogen; and $R^5$ is (tertiary amino)(lower alkoxy) of the polymethyleneimine type. Within particularly preferred embodiments, $R^1$ is in the 7-position and is lower alkoxy, particularly methoxy; each of $R^2$ and $R^3$ is methyl, $R^4$ is hydrogen, and $R^5$ is in the 4position and is a (tertiary amino)(lower alkoxy) radical such as 2-(pyrrolidin-1-yl) ethoxy. To be included by this invention are all pharmaceutically acceptable salts of the mentioned compounds of formula I.

It is preferred to use the compounds of formula I in the transconfiguration. These compounds may be used as racemic mixtures, or the isolated stereoisomers, e.g. d- or l-enantiomers, may be used. The trans-l-enantiomers are more preferred.

A particularly preferred compound for use within the present invention is centchroman consisting of l-centchroman and d-centchroman. Probably, l-centchroman has the formula IV.

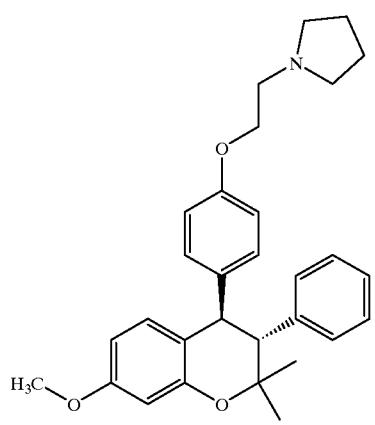

(IV)

3,4diarylchromans are prepared according to known methods, such as those disclosed in U.S. Pat. No. 3,340,276 to Carney et al., U.S. Pat. No. 3,822,287 to Bolger, and Ray et al., J.Med.Chem. 19 (1976), 276–279, the contents of which are incorporated herein by reference. Conversion of the cis isomer to the trans configuration by means of an organometallic base-catalyzed rearrangement is disclosed in U.S. Pat. No. 3,822,287. The optically active d- and l-enantiomers may be prepared as disclosed by Salman et al. in U.S. Pat. No. 4,447,622 (incorporated herein by reference) by forming an optically active acid salt which is subjected to alkaline hydrolysis to produce the desired enantiomer. If $R^2$ is different from $R^3$ and $R^4$ is different from $R^5$, the general formula I covers 8 optical isomers.

Within the present invention, 3,4-diarylchromans of formula I may be prepared in the form of pharmaceutically acceptable salts, especially acid-addition salts, including salts of organic acids and mineral acids. Examples of such salts include salts of organic acids such as formic acid, fumaric acid, acetic acid, propionic acid, glycolic acid, lactic acid, pyruvic acid, oxalic acid, succinic acid, malic acid, tartaric acid, citric acid, benzoic acid, salicylic acid and the like. Suitable inorganic acid-addition salts include salts of hydrochloric, hydrobromic, sulphuric and phosphoric acids and the like. The acid addition salts may be obtained as the direct products of compound synthesis. In the alternative, the free base may be dissolved in a suitable solvent containing the appropriate acid, and the salt isolated by evaporating the solvent or otherwise separating the salt and solvent.

3,4diarylchromans of formula I and their salts are useful within human and veterinary medicine, for example, in the treatment of patients suffering from obesity. For use within the present invention, 3,4diaryl-chromans of formula I and their pharmaceutically acceptable salts are formulated with a pharmaceutically acceptable carrier to provide a medicament for parenteral, oral, nasal, rectal, subdermal or intradermal or transdermal administration according to conventional methods. Formulations may further include one or more diluents, fillers, emulsifiers, preservatives, buffers, excipients, etc. and may be provided in such forms as liquids, powders, emulsions, suppositories, liposomes, transdermal patches, controlled release, dermal implants, tablets, etc. One skilled in this art may formulate the compounds of formula I in an appropriate manner, and in accordance with accepted practices, such as those disclosed in Remington's Pharmaceutical Sciences, Gennaro, ed., Mack Publishing Co., Easton, Pa., 1990.

Oral administration is preferred. Thus, the active compound of formula I is prepared in a form suitable for oral administration, such as a tablet or capsule. Typically, a pharmaceutically acceptable salt of the compound of formula I is combined with a carrier and moulded into a tablet. Suitable carriers in this regard include starch, sugars, dicalcium phosphate, calcium stearate, magnesium stearate and the like. Such compositions may further include one or more auxiliary substances, such as wetting agents, emulsifiers, preservatives, stabilizers, colouring additives, etc.

Pharmaceutical compositions containing a compound of formula I may be administered one or more times per day or week. An effective amount of such a pharmaceutical composition is the amount that provides a clinically significant effect against obesity. Such amounts will depend, in part, on the particular condition to be treated, age, weight, and general health of the patient, and other factors evident to those skilled in the art.

The pharmaceutical compositions containing a compound of formula I may be administered in unit dosage form one or more times per day or week. In the alternative, they may be provided as controlled release formulations suitable for dermal implantation. Implants are formulated to provide release of active compound over the desired period of time, which can be up to several years. Controlled-release formulations are disclosed by, for example, Sanders et a., J.Pharm-.Sci. 73 (1964), 1294–1297, 1984; U.S. Pat. No. 4,489,056; and U.S. Pat. No. 4,210,644, which are incorporated herein by reference.

Examples of preferred compounds of formula I are centchroman as a racemic mixture and as l-centchroman and d-centchroman. Furthermore, 3,4-trans-2,2-dimethyl-3-phenyl-4-[4-(2-(pyrrolidin-1-yl)ethoxy)phenyl]-7-hydroxychroman is a preferred compound. A more preferred compound is l-3,4-trans-2,2-dimethyl-3-phenyl-4-[4-(2-(pyrrolidin- 1-yl)ethoxy)phenyl]-7-methoxychroman.

The present invention is further illustrated by the following examples which, however, are not to be construed as limiting the scope of protection.

The features disclosed in the foregoing description and in the following examples may, both separately and in any combination thereof, be material for realising the invention in diverse forms thereof.

EXAMPLES

Test 1

The effects of l-centchroman on rabbit weight gain have been investigated in cholesterol fed rabbits. Thirty sexually mature female New Zealand White rabbits (weight range of 3000–3550 g body weight) were obtained. The animals were housed in cages 35 by 45 cm, one in each cage with ad libitum access to water. Room temperature was kept at 18±0,5° C. with a minimum relative humidity of 40%. One week before the medical treatment was started the animals were bilaterally ovariectomized during pentobarbital anaesthesia. Following recovery and a one week recovery period subcutaneous treatment was started in three groups: Vehicle, 17-β-estradiol (0.5 mg/kg or I-centchroman 7.5 mg/kg. The doses were administered three times per week for 4 weeks. Throughout the experiment the animals were subject to food restriction by only being offered 100 g of food every day. All rats ate all of their food each day. At the beginning, once per week during the treatment period and at the end of the experiment the rabbits were weighed and the weight gain throughout the period was determined. As shown in Table 1 I-centchroman reduced weight gain significantly compared to the vehicle treated animals and to the level of estrogen treated animals.

TABLE 1

Weight gain in constant fed and drug treated rabbits

| Treatment | Weight gain (g) |
|---|---|
| Placebo | 255 ± 20 |
| Estrogen | 246 ± 34 |
| I-centchroman | 38 ± 28* |

Values are mean ± SEM.
*indicate significant reduction of weight gain compared to placebo treated animals; p < 0.001.

In addition to the demonstrated benefits of the compound used in the methods of the present invention, no deleterious toxicological effects were observed.

Test 2

Twenty eight genetically obese male mice (ob/ob mice) are bought from Mollegaards Breeding Center, LI. Skensved, Denmark. The animals are housed in metal hanging cages in groups of 3 or 4 per cage and have ad libitum access to food and water for one week of acclimation. Room temperature is maintained at 21±0.5° C. with a relative humidity of 40%. The photoperiod in the room is 12 hours light and 12 hours dark.

After a one week acclimation period dosing with the test compounds is initiated. The amount of compound administered is from 0.001 to 100 mg/day and the period of administration is 1 month. The compound is given by isotonic injections intraperitoneally twice a week. The food consumption is measured daily and the animals are weighed two times per week during the treatment period.

Test 3

The same procedure is used as in Test 2, except the period of administration is 3 months.

Test 4

The same procedure is used as in Test 2, except the period of administration is 6 months.

Test 5

Between 3 and 20 obese (according to the criteria mentioned above) women are administered a compound of the present invention. The amount of compound administered is from 0.1 to 1000 mg/day, and the period of treatment is 6 months.

The women are observed during the period of administration, and up to 3 months after discontinuance of administration, for effects on their obesity.

Test 6

The same procedure is used as in Test 5, except the period of administration is 1 year.

Test 7

The same procedure is used as in Test 5, except between 3 and 20 obese males are used.

Test 8

The same procedure is used as in Test 7, except the period of administration is 1 year.

What is claimed:

1. A method for the treatment of obesity comprising administering to a patient in need of such treatment the isolated compound 1-3,4-trans-2,2-dimethy-3-phenyl-4-[4-(2-(pyrrolidin-1-yl)ethoxy)phenyl]-7-methoxychroman in an amount less than about 25 mg/kg patient per day but in anamount suffcient to treat obesity.

2. The method according to claim 1 wherein said compound is administered orally.

3. The method according to claim 1 wherein said compound is administered in the form of a dermal implant.

* * * * *